United States Patent [19]
Bandman et al.

[11] Patent Number: 5,874,224
[45] Date of Patent: Feb. 23, 1999

[54] GROWTH FACTOR RECEPTOR BINDING PROTEIN

[75] Inventors: Olga Bandman, Mountain View; Anthony P. Diegidio, Redwood City, both of Calif.

[73] Assignee: Incyte Pharmaceuticals, Inc., Palo Alto, Calif.

[21] Appl. No.: 815,176

[22] Filed: Mar. 11, 1997

[51] Int. Cl.$^6$ .............................. C12N 15/12; C12N 5/10; C12N 15/63
[52] U.S. Cl. ........................... 435/6; 435/325; 435/320.1; 435/252.3; 435/69.1; 536/23.5; 536/24.3
[58] Field of Search .................................. 536/23.5, 24.3; 435/325, 320.1, 252.3, 6, 69.1

[56] References Cited

PUBLICATIONS

D'Alessio, GenBank/EMBL record. Accession No. U14626, Definition: Cloning Vector pSVsport 1 beta lactamese gene. 24 May 1995.
Hillies et al. EST–STS–Two Record. Accession No. RO2185. Definition: ye87g05.1 Homosapiens cDNA clone 124760 3' similar to SP. JT0664. 31 Mar. 1995.
Bowie et al. Science 247, 1306–1310, 1990.
Frantz et al. J. Biol. Chem. 272, 2659–2667, 1997.
Suen, K., et al., "Molecular Cloning of the mouse grb2 gene: Differential interaction of the grb2 adaptor protein with epidermal growth factor and nerve receptors," *Molecular and Cellular Biology*, vol. 13, No. 9, pp. 5500–5512, XP002064590 Sep. 1993.
Marra, M., et al., "The WashU–HHMI Mouse 3NbMS mus musculus cDNA clone 619186 5'," *EMBL Database Entry MMAA75718*, Accession No. AA175718, XP002064591, Feb. 18, 1997.
Lowenstein, E.J. et al., "The SH2 and SH3 Domain–Containing Protein GRB2 Links Receptor Tyrosine Kinases to ras Signaling." *Cell* (1992) 70:431–442.
Matuoka, K., et al., "Cloning of ASH, a ubiquitous protein composed of one Src homology region (SH) 2 and two SH3 domains, from human and rat cDNA libraries." *Proc. Natl. Acad. Sci.* (1992) 89:9015–9019. (GI 55763).
Egan, S.E., et al., "Association of Sos Ras exchange protein with Grb2 is implicated in tyrosine kinase signal transduction and transformation." *Nature* (1993) 363:45–51.
Buday, L., et al., "Epidermal Growth Factor Regulates p21$^{ras}$ through the Formation of a Complex of Receptor, Grb2 Adapter Protein, and Sos Nucleotide Exchange Factor." *Cell* (1993) 73:611–620.
Clark, S.G., et al., "C. elegans cell–signalling gene sem–5 encodes a protein with SH2 and SH3 domains." *Nature* (1992) 356:340–344. (GI 134425).

*Primary Examiner*—Elizabeth Kemmerer
*Attorney, Agent, or Firm*—Lucy J. Billings; Sheela Mohan-Peterson; Leanne C. Price

[57] ABSTRACT

The present invention provides a human growth factor receptor binding protein (GRBP) and polynucleotides which encode GRBP. The invention also provides expression vectors, host cells, agonists, antisense molecules, antibodies, or antagonists. The invention also provides methods for producing GRBP and for treating disorders associated with expression of GRBP.

10 Claims, 5 Drawing Sheets

```
                  9            18            27            36            45            54
5' NNN GGG GCA GTG CAA GCT TGC ATG CCT GCA GGT CGA CTC TAG AGG ATC CCG GAC 63            72            81            90            99           108
    TCT AGC CTA GGC TTT TGC AAA AAG CTA TTT AGG TGA CAC TAT AGA AGG TAC GCC 117           126           135           144           153           162
    TGC AGG TAC CGG TCC GGA ATT CCC GGG TCG ACC CAC GCG TCC GGG AGG AGG GAG 171           180           189           198           207           216
    TAA GAG GTG GGG AGG AGG AGG CAC AGT TAA TGG ATC TGT AAA CTT GCA CCC TCT 225           234           243           252           261           270
    TTC AGA GTG GTA CAT GGA AGA CAG CAC AAA GTG GAT CCA TAC TCT GAA ATG CAG 279           288           297           306           315           324
    TAA CTC TGG TGC TTG AAT TTG TCT CCC TTC TTG CCA GAA AGG ATT CTA ATA ACT 333           342           351           360           369           378
    CGG TGT CAA AGC CAA GAC ATA AAC TCA ACC CCT TCT CTT CCA AAA GCT TCA CGT 387           396           405           414           423           432
    TAC AGC ATG GAA GCT GTT GCC AAG TTT GAT TTC ACT GCT TCA GGT GAG GAT GAA
                    M   E   A   V   A   K   F   D   F   T   A   S   G   E   D   E 441           450           459           468           477           486
    CTG AGC TTT CAC ACT GGA GAT GTT TTG AAG ATT TTA AGT AAC CAA GAG GAG TGG
     L   S   F   H   T   G   D   V   L   K   I   L   S   N   Q   E   E   W 495           504           513           522           531           540
    TTT AAG GCG GAG CTT GGG AGC CAG GAA GGA TAT GTG CCC AAG AAT TTC ATA GAC
     F   K   A   E   L   G   S   Q   E   G   Y   V   P   K   N   F   I   D 549           558           567           576           585           594
    ATC CAG TTT CCC AAA TGG TTT CAC GAA GGC CTC TCT CGA CAC CAG GCA GAG AAC
     I   Q   F   P   K   W   F   H   E   G   L   S   R   H   Q   A   E   N 603           612           621           630           639           648
    TTA CTC ATG GAC AAG GAG GTT GGC TTC TTC ATC ATC CGG GCC AGC CAG AGC TCC
     L   L   M   D   K   E   V   G   F   F   I   I   R   A   S   Q   S   S
```

FIGURE 1A

```
       657         666         675         684         693         702
CCA GGG GAC TTC TCC ATC TCT GTC AGG CAT GAG GAT GAC GTT CAA CAC TTC AAG
 P   G   D   F   S   I   S   V   R   H   E   D   D   V   Q   H   F   K 711         720         729         738         747         756
GTC ATG CGA GAC AAC AAG GGT AAT TAC TTT CTG TGG ACT GAG AAG TTT CCA TCC
 V   M   R   D   N   K   G   N   Y   F   L   W   T   E   K   F   P   S 765         774         783         792         801         810
CTA AAT AAG CTG GTA GAC TAC TAC AGG ACA AAT TCC ATC TCC AGA CAG AAG CAG
 L   N   K   L   V   D   Y   Y   R   T   N   S   I   S   R   Q   K   Q 819         828         837         846         855         864
ATC TTC CTT AGA GAC AGA ACC CGA GAA GAC CAG GGT CAC CGG GGC AAC AGC CTG
 I   F   L   R   D   R   T   R   E   D   Q   G   H   R   G   N   S   L 873         882         891         900         909         918
GAC CGG AGG TCC CAG GGA GGC CCA CAC CTC AGT GGG GCT GTG GGG GAA GAA ATC
 D   R   R   S   Q   G   G   P   H   L   S   G   A   V   G   E   E   I 927         936         945         954         963         972
CGA CCT TCG ATG AAC CGG AAG CTG TCG GAT CAC CCC CCG ACC CTT CCC CTG CAG
 R   P   S   M   N   R   K   L   S   D   H   P   P   T   L   P   L   Q 981         990         999        1008        1017        1026
CAG CAC CAG CAC CAG CCA CAG CCT CCG CAA TAT GCC CCA GCG CCC CAG CAG CTG
 Q   H   Q   H   Q   P   Q   P   P   Q   Y   A   P   A   P   Q   Q   L 1035        1044        1053        1062        1071        1080
CAG CAG CCC CCA CAG CAG CGA TAT CTG CAG CAC CAC CAT TTC CAC CAG GAA CGC
 Q   Q   P   P   Q   Q   R   Y   L   Q   H   H   H   F   H   Q   E   R 1089        1098        1107        1116        1125        1134
CGA GGA GGC AGC CTT GAC ATA AAT GAT GGG CAT TGT GGC ACC GGC TTG GGC AGT
 R   G   G   S   L   D   I   N   D   G   H   C   G   T   G   L   G   S 1143        1152        1161        1170        1179        1188
GAA ATG AAT GCG GCC CTC ATG CAT CGG AGA CAC ACA GAC CCA GTG CAG CTC CAG
 E   M   N   A   A   L   M   H   R   R   H   T   D   P   V   Q   L   Q 1197        1206        1215        1224        1233        1242
GCG GCA GGG CGA GTG CGG TGG GCC CGG GCG CTG TAT GAC TTT GAG GCC CTG GAG
 A   A   G   R   V   R   W   A   R   A   L   Y   D   F   E   A   L   E 1251        1260        1269        1278        1287        1296
GAT GAC GAG CTG GGG TTC CAC AGC GGG GAG GTG GTG GAG GTC CTG GAT AGC TCC
 D   D   E   L   G   F   H   S   G   E   V   V   E   V   L   D   S   S
```

FIGURE 1B

```
         1305          1314          1323          1332          1341          1350
AAC CCA TCC TGG TGG ACC GGC CGC CTG CAC AAC AAG CTG GGC CTC TTC CCT GCC
 N   P   S   W   W   T   G   R   L   H   N   K   L   G   L   F   P   A 1359          1368          1377          1386          1395          1404
AAC TAC GTG GCA CCC ATG ACC CGA TAA ACT CTT CAG GGG ACA GAA GCT TTT TGT
 N   Y   V   A   P   M   T   R 1413          1422          1431          1440          1449          1458
CTG GAG CTG CCC ACA AGA AAG AGG GCA AGG AAG AAA GGC TGG ACT CCA TGA CTA 1467          1476          1485          1494          1503          1512
TAT ATA CAT ACA TCT ATC TAC ATC TGC CTG TGT ACA CAC ACA ACT TTT TAT ACT 1521          1530          1539          1548          1557          1566
AGT AAT TTA TTG CAA TTG GGC TGG TAA TTA GTT GAT GCA AAA GGG AAC TCA GGT 1575          1584          1593          1602          1611          1620
GGA GAA TAA TAT TGA CAC TTG CTT TTC TGC CCC CCT CAG GGG TGT GTG AAA GGC 1629          1638          1647          1656
AGT GGG GGA GTT GGG AGG GGG GCA GGG AAA TGA AAT GGA GTT TT 3'
```

```
  1  M E A V A K F D F T A S G E D E L S F H T G D V L K I L S N Q - - E E W F K A E   GRBP
  1  M E A I A K Y D F K A T A D D E L S F K R G D I L K V L N E E C D Q N W Y K A E   g181976
  1  M E A I A K Y D F K A T A D D E L S F K R G D I L K V L N E E C D Q N W Y K A E   g55763
  1  M E A V A E H D F Q A G S P D E L S F K R G N T L K V L N K D E D P H W Y K A E   g134425

39  L G S Q E G Y V P K N F I D I Q F P K W F H E G L S R H Q A E N L L M D K E V - -  GRBP
 41  L N G K D G F I P K N Y I E M K P H P W F F G K I P R A K A E E M L S K Q R - H   g181976
 41  L N G K D G F I P K N Y I E M K P H P W F F G K I P R A K A E E M L S K Q R - H   g55763
 41  D G N E G F I P S N Y I R M T E C N W Y L G K I T R N D A E V L L K K P T V R     g134425

78  - G F F I R A Q S S P G D F S I S V R H E D D V Q H F K V M R D N K G N Y F       GRBP
 80  D G A F L I R E S E S A P G D F S L S V K F G N D V Q H F K V L R D G A G K Y F   g181976
 80  D G A F L I R E S E S A P G D F S L S V K F G N D V Q H F K V L R D G A G K Y F   g55763
 81  D G H F L V R Q C E S S P G E F S I S V R F Q D S V Q H F K V L R D Q N G K Y Y   g134425

117  L W T E K F P S L N K L V D Y Y R T N S I S R Q K Q I F L R D R T R E D Q G H R   GRBP
120  L W V V K F N S L N E L V D Y H R S T S V S R N Q Q I H F L R D I E - - - - - -   g181976
120  L W V V K F N S L N E L V D Y H R S T S V S R N Q Q I F L R D I E - - - - - -     g55763
121  L W A V K F N S L N E L V A Y H R T A S V S R T H T H L L S D M N - - - - - - -   g134425

157  G N S L D R R S Q G G P H L S G A V G E E I R P S M N R K L S D H P P T L P L Q   GRBP
153  - - - - - - - - - - - - - - - - - - - - - - - - - - - - - - - - - - - - - -     g181976
153  - - - - - - - - - - - - - - - - - - - - - - - - - - - - - - - - - - - - - -     g55763
154  - - - - - - - - - - - - - - - - - - - - - - - - - - - - - - - - - - - - - -     g134425
```

| Pos | Sequence | Label |
|---|---|---|
| 197 | Q H Q H Q P Q P P Q Y A P A P Q Q L Q P P Q Q R Y L Q H H H F H Q E R R G G S | GRBP |
| 153 | - - - - - - - - - - - - - - - - - Q V P Q Q P T Y V Q - - - - - - - - - | g181976 |
| 153 | - - - - - - - - - - - - - - - - - Q V P Q Q P T Y V Q - - - - - - - - - | g55763 |
| 154 | - - - - - - - - - - - - - - - - - - V E T K F V Q - - - - - - - - - | g134425 |
| 237 | L D I N D G H C G T G L G S E M N A A L M H R R H T D P V Q L Q A A G R V R W A | GRBP |
| 163 | - - - - - - - - - - - - - - - - - - - - - - - - - - - - - - - - | g181976 |
| 163 | - - - - - - - - - - - - - - - - - - - - - - - - - - - - - - - - | g55763 |
| 161 | - - - - - - - - - - - - - - - - - - - - - - - - - - - - - - - - | g134425 |
| 277 | R A L Y D F E A L E D D E L G F H S G E V V E V L D S S N P S W T G R L H N K | GRBP |
| 163 | - A L F D F D P Q E D G E L G F R R G D F I H V M D N S D P N W W K G A C H G Q | g181976 |
| 163 | - A L F D F D P Q E D G E L G F R R G D F I H V M D N S D P N W W K G A C H G Q | g55763 |
| 161 | - A L F D F N P Q E S G E L A F K R G D V I T L I N K D D P N W W E G Q L N N R | g134425 |
| 317 | L G L F P A N Y V A P M T R | GRBP |
| 202 | T G M F P R N Y V T P V N R N V | g181976 |
| 202 | T G M F P R N Y V T P V N R N V | g55763 |
| 200 | R G I F P S N Y V C P Y N S N K S N S N V A P G F N F G N | g134425 |

FIGURE 2B

GROWTH FACTOR RECEPTOR BINDING PROTEIN

FIELD OF THE INVENTION

This invention relates to nucleic acid and amino acid sequences of a novel growth factor receptor binding protein and to the use of these sequences in the diagnosis, prevention, and treatment of cancer, immunological disorders and disorders of the sympathetic nervous system.

BACKGROUND OF THE INVENTION

Signal transduction is the general process by which cells repond to extracellular signals (hormones, neurotransmitters, growth and differentiation factors, etc.) through a cascade of biochemical reactions. The process begins with the binding of the signal molecule to a cell membrane receptor and ends with the activation of an intracellular target molecule. Such processes regulate all types of cell functions including cell proliferation, differentiation, and gene transcription, as well as oncogenic transformation.

Many growth factor receptors, including epidermal growth factor, platelet-derived growth factor, and fibroblast growth factor contain intrinsic protein kinase activities. When the polypeptide growth factor binds to the receptor, it triggers the autophosphorylation of a tyrosine residue on the receptor. It is believed that these phosphorylated sites are recognition sites for the binding of other cytoplasmic signaling proteins in the signaling pathway that eventally links the initial receptor activation at the cell surface to the activation of a specific intracellular target molecule. These signaling proteins contain a common domain refered to as a src homology 2 (SH2) domain. SH2 domains are found in a variety of signaling molecules and oncogenic proteins such as phospholipase C-γ, Ras GTP-ase activating protein, and pp60$^{c-src}$ (Lowenstein, E. J. et al. (1992) Cell 70:431–42).

A subfamily of these receptor binding, cell signaling proteins has been found in humans and is called Grb2 (growth factor receptor binding protein). Grb2 homologs have been identified in rat (ASH), C. elegans (Sem-5), and Drosophila (Drk) (Lowenstein et al., supra; Matuoka, K. et al. (1992) Proc, Natl. Acad. Sci. 89:9015–19). Grb2 and its homologs contain an SH2 domain flanked by SH3 (src-homology 3) domains. The homology between these domains from species to species ranges between 45 and 60% indicating an evolutionarily well conserved family of proteins.

Grb2 and its homologs appear to function in the Ras signaling pathway by mediating an interaction between the phosphorylated EGF receptor and a Ras activating protein that converts GDP to bound GTP (Egan, S. E. et al. (1993) Nature 363:45–48; Laszlo, B. and Downward, J. (1993) Cell 73:611–20). Activated Ras stimulates normal growth and differentiation processes in some cell types and oncogenic transformation and the development of cancer in others. Binding studies conducted with isolated domains from Grb proteins have determined that binding of the SH2 domain of Grb to the phosphotyrosine region of the EGF receptor and the binding of the two flanking SH3 domains to the Ras activating protein is simultaneous. Specific amino acid substitutions in the SH2 and SH3 domains of Grb proteins have further defined the important functional amino acid residues (Matuoka, et al., supra; Egan, et al., supra).

The discovery of a novel growth factor receptor binding protein provides a means to investigate cell growth and differentiation processes under normal and disease conditions. Such molecules related to a growth factor receptor binding protein satisfy a need in the art by providing new diagnostic or therapeutic compositions useful in cancer, immunological disorders and disorders of the sympathetic nervous system.

SUMMARY OF THE INVENTION

The present invention features a novel growth factor receptor binding protein hereinafter designated GRBP and characterized as having similarity to growth factor receptor binding proteins.

Accordingly, the invention features a substantially purified GRBP having the amino acid sequence shown in SEQ ID NO:1.

One aspect of the invention features isolated and substantially purified polynucleotides that encode GRBP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode GRBP. The present invention also features antibodies which bind specifically to GRBP, and pharmaceutical compositions comprising substantially purified GRBP. The invention also features the use of agonists and antagonists of GRBP. The invention also provides methods for producing GRBP and for treating disorders associated with expression of GRBP.

BRIEF DESCRIPTION OF THE FIGURES

FIGS. 1A, 1B, and 1C show the amino acid sequence (SEQ ID NO:1) and nucleic acid sequence (SEQ ID NO:2) of GRBP. The alignment was produced using MACDNASIS PRO software (Hitachi Software Engineering Co., Ltd., San Bruno, Calif.).

FIGS. 2A and 2B show the amino acid sequence alignments among GRBP (SEQ ID NO:1), Grb2 (GI 181976; SEQ ID NO:3), ASH (GI 55763; SEQ ID NO:4), and Sem-5 (GI 134425; SEQ ID NO:5). The alignment was produced using the multisequence alignment program of DNASTAR software (DNASTAR Inc. Madison Wis.).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

GRBP, as used herein, refers to the amino acid sequences of substantially purified GRBP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of GRBP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic GRBP, or any oligopeptide thereof, to induce a specific immune response in appropriate animals or cells and to bind with specific antibodies.

The term "agonist", as used herein, refers to a molecule which, when bound to GRBP, causes a change in GRBP which modulates the activity of GRBP. Agonists may include proteins, nucleic acids, carbohydrates, or any other molecules which bind to GRBP.

The terms "antagonist" or "inhibitor", as used herein, refer to a molecule which, when bound to GRBP, inhibits the biological or immunological activity of GRBP. Antagonists and inhibitors may include proteins, nucleic acids, carbohydrates, or any other molecules which bind to GRBP.

The term "modulate", as used herein, refers to a change or an alteration in the biological activity of GRBP. Modulation may be an increase or a decrease in protein activity, a change in binding characteristics, or any other change in the biological, functional or immunological properties of GRBP.

The term "mimetic", as used herein, refers to a molecule, the structure of which is developed from knowledge of the structure of GRBP or portions thereof and, as such, is able to effect some or all of the actions of growth factor receptor binding protein-like molecules.

The term "derivative", as used herein, refers to the chemical modification of a nucleic acid encoding GRBP or the encoded GRBP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous."The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm–5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human GRBP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding GRBP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding GRBP in a sample and thereby correlates with expression of the transcript from the polynucleotide encoding the protein.

"Alterations" in the polynucleotide of SEQ ID NO:2, as used herein, comprise any alteration in the sequence of polynucleotides encoding GRBP including deletions, insertions, and point mutations that may be detected using hybridization assays. Included within this definition is the detection of alterations to the genomic DNA sequence which encodes GRBP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding GRBP (e.g., using fluorescent in situ hybridization [FISH] to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind GRBP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human growth factor receptor binding protein (GRBP), the polynucleotides encoding GRBP, and the use of these compositions for the diagnosis, prevention, or treatment of cancer, immunological disorders, and disorders of the sympathetic nervous system.

Nucleic acids encoding the human GRBP of the present invention were first identified in Incyte Clone 1291904 from the paraganglion cDNA library PGANNOT03 through a computer-generated search for amino acid sequence alignments, and a consensus sequence, SEQ ID NO:2, was derived from the extension and resequencing of this clone.

In one embodiment, the invention encompasses a polypeptide comprising the amino acid sequence of SEQ ID NO:1, as shown in FIGS. 1A, 1B and 1C. GRBP is 330 amino acids in length has chemical and structural homology with the growth factor receptor binding proteins Grb2 (GI 181976; SEQ ID NO:3), ASH (GI 55763; SEQ ID NO:4), and Sem-5 (GI 134425; SEQ ID NO:5). In particular, GRBP shares 53% identity with Grb2 and ASH, and 48% identity with Sem-5. This degree of homology is consistent with that exhibited between other members of the family. The SH2 binding domain of GRBP extends from approximately residue W58 to is D147, and the two SH3 domains extend from approximately A5 to K57 (SH3N) and from A278 to Y324 (SH3C), respectively. Within these domains, amino acid substitutions have identified P47 in the SH3N domain, W58 in the SH2 domain, and G318 in the SH3C domain as being essential for the binding activities of the proteins. The domains and all three residues are conserved in GRBP, Grb2, ASH, and Sem-5. In addition, a 17-amino acid sequence extending from F809 to V96 in GRBP has been identified as highly conserved and is approximately 70% identical between GRBP and Grb2. The greatest single difference between GRBP and other Grb proteins is the presence of a sequence of approximately 125 amino acids extending between T149 and R277 of GRBP that is located between the SH2 and SH3C regions of GRBP. This sequence may confer a novel structural conformation or additional binding properties not found in other Grb proteins. Northern analysis indicates GRBP to be widely distributed in tissues as has been found with Grb2 and ASH. In particular, GRBP is found in cancerous tissues and immortalized cell lines (32%), smooth muscle tissues and tissues associated with the sympathetic nervous system (paraganglion and adrenal gland) (32%), and tissues associated with inflammation and the immune response (20%).

The invention also encompasses GRBP variants. A preferred GRBP variant is one having at least 80%, and more preferably 90%, amino acid sequence similarity to the GRBP amino acid sequence (SEQ ID NO:1). A most preferred GRBP variant is one having at least 95% amino acid sequence similarity to SEQ ID NO:1.

The invention also encompasses polynucleotides which encode GRBP. Accordingly, any nucleic acid sequence which encodes the amino acid sequence of GRBP can be used to generate recombinant molecules which express GRBP. In a particular embodiment, the invention encompasses the polynucleotide comprising the nucleic acid sequence of SEQ ID NO:2 as shown in FIGS. 1A, 1B, 1C.

It will be appreciated by those skilled in the art that as a result of the degeneracy of the genetic code, a multitude of nucleotide sequences encoding GRBP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring GRBP, and all such variations are to be considered as being specifically disclosed.

Although nucleotide sequences which encode GRBP and its variants are preferably capable of hybridizing to the nucleotide sequence of the naturally occurring GRBP under appropriately selected conditions of stringency, it may be advantageous to produce nucleotide sequences encoding GRBP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GRBP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode GRBP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding GRBP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding GRBP which are encompassed by the invention include deletions, insertions, or substitutions of different nucleotides resulting in a polynucleotide that encodes the same or a functionally equivalent GRBP. The encoded protein may also contain deletions, insertions, or substitutions of amino acid residues which produce a silent change and result in a functionally equivalent GRBP. Deliberate amino acid substitutions may be made on the basis of similarity in polarity, charge, solubility, hydrophobicity, hydrophilicity, and/or the amphipathic nature of the residues as long as the biological activity of GRBP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding GRBP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (U.S. Biochemical Corp, Cleveland, Ohio), TAQ polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton MICRO LAB 2200 (Hamilton, Reno, Nev.), Peltier thermal cycler (PTC200; MJ Research, Watertown, Mass.) and ABI 377 DNA sequencers (Perkin Elmer).

The nucleic acid sequences encoding GRBP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTER FINDER™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode GRBP, or fusion proteins or functional equivalents thereof, may be used in recombinant DNA molecules to direct expression of GRBP in appropriate host cells. Due to the inherent degeneracy of the genetic code, other DNA sequences which encode substantially the same or a functionally equivalent amino acid sequence may be produced and these sequences may be used to clone and express GRBP.

As will be understood by those of skill in the art, it may be advantageous to produce GRBP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter GRBP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding GRBP may be ligated to a heterologous sequence to encode a fusion protein. For example, to screen peptide libraries for inhibitors of GRBP activity, it may be useful to encode a chimeric GRBP protein that can be recognized by a commercially available antibody. A fusion protein may also be engineered to contain a cleavage site located between the GRBP encoding sequence and the heterologous protein sequence, so that GRBP may be cleaved and purified away from the heterologous moiety.

In another embodiment, sequences encoding GRBP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of GRBP, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of GRBP, or any part thereof, may be altered during direct synthesis and/or combined using chemical methods with sequences from other proteins, or any part thereof, to produce a variant polypeptide.

In order to express a biologically active GRBP, the nucleotide sequences encoding GRBP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding GRBP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding GRBP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding GRBP, vectors based on SV40 or EBV may be used with an appropriate selectable marker.

In bacterial systems, a number of expression vectors may be selected depending upon the use intended for GRBP. For example, when large quantities of GRBP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding GRBP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding GRBP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express GRBP. For example, in one such system, *Autographa californica* nuclear polyhedrosis virus (ACNPV) is used as a vector to express foreign genes in *Spodoptera frugiperda* cells or in Trichoplusia larvae. The sequences encoding GRBP may be cloned into a non-essential region of the virus, such as the polyhedrin gene, and placed under control of the polyhedrin promoter. Successful insertion of GRBP will render the polyhedrin gene inactive and produce recombinant virus lacking coat protein. The recombinant viruses may then be used to infect, for example, *S. frugiperda* cells or Trichoplusia larvae in which GRBP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding GRBP may be ligated into an adenovirus transcription/translation complex consisting of the late promoter and tripartite leader sequence. Insertion in a non-essential E1 or E3 region of the viral genome may be used to obtain a viable virus which is capable of expressing GRBP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding GRBP. Such signals include the ATG initiation codon and adjacent sequences. In cases where sequences encoding GRBP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express GRBP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131). .

Although the presence/absence of marker gene expression suggests that the gene of interest is also present, its presence and expression may need to be confirmed. For example, if the sequence encoding GRBP is inserted within a marker gene sequence, recombinant cells containing sequences encoding GRBP can be identified by the absence of marker gene function. Alternatively, a marker gene can be placed in tandem with a sequence encoding GRBP under the control of a single promoter. Expression of the marker gene in response to induction or selection usually indicates expression of the tandem gene as well.

Alternatively, host cells which contain the nucleic acid sequence encoding GRBP and express GRBP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding GRBP can be detected by DNA-DNA or DNA-RNA hybridization or amplification using probes or portions or fragments of polynucleotides encoding GRBP. Nucleic acid amplification based assays involve the use of oligonucleotides or oligomers based on the sequences encoding GRBP to detect transformants containing DNA or RNA encoding GRBP. As used herein, "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of GRBP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on GRBP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GRBP include oligolabeling, nick translation, end-labeling or PCR amplification using a labeled nucleotide. Alternatively, the sequences encoding GRBP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison Wis.); and U.S. Biochemical Corp. Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding GRBP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode GRBP may be designed to contain signal sequences which direct secretion of GRBP through a prokaryotic or eukaryotic cell membrane. Other recombinant constructions may be used to join sequences encoding GRBP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and GRBP may be used to facilitate purification. One such expression vector provides for expression of a fusion protein containing GRBP and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263–281) while the enterokinase cleavage site provides a means for purifying GRBP from the fusion protein. A discussion of vectors which contain fusion proteins is provided in Kroll, D. J. et al. (1993; DNA Cell Biol. 12:441–453).

In addition to recombinant production, fragments of GRBP may be produced by direct peptide synthesis using solid-phase techniques Merrifield J. (1963) J. Am. Chem. Soc. 20 85:2149–2154). Protein synthesis may be performed using manual techniques or by automation. Automated synthesis may be achieved, for example, using an Applied Biosystems 431A peptide synthesizer (Perkin Elmer). Various fragments of GRBP may be chemically synthesized separately and combined using chemical methods to produce the full length molecule.

THERAPEUTICS

Chemical and structural homology exists among GRBP and growth factor receptor binding proteins from human (Grb2), rat (ASH), and *C. elegans* (Sem-5). In addition, northern analysis shows that GRBP is expressed in cancerous tissues and immortalized cell lines, smooth muscle tissues, and tissues associated with the sympathetic nervous system, and tissues associated with inflammation and the immune reponse. Therefore, GRBP appears to be associated with the development of cancer, immunological disorders, and disorders of the sympathetic nervous system. In particular, increased expression or activity of GRBP may be associated with cancer and immune disorders, while decreased expression or activity of GRBP may be associated with sympathetic nervous system disorders.

Therefore, in one embodiment, GRBP or a fragment or derivative thereof may be administered to a subject to treat a disorder of the sympathetic nervous system. Such disorders may include, but are not limited to, hypertension, myocardial infarction, cardiovascular shock, angina, arrhythmias, asthma, migraine, anaphylactic shock, Cushing's syndrome, hypoglycemia, and pheochromocytoma.

In another embodiment, a vector capable of expressing GRBP, or a fragment or a derivative thereof, may also be administered to a subject to treat any of the disorders of the sympathetic nervous system listed above.

In another embodiment, the complement of the polynucleotide encoding GRBP or an antisense molecule may be administered to a subject to treat or prevent cancer. Cancers may include, but are not limited to, adenocarcinoma, sarcoma, melanoma, lymphoma, leukemia, and myeloma. In particular, they include cancer of the stomach, lung, heart, colon, cervix, ovaries, blood, intestine, prostate, uterus, breast, liver, spleen, brain, bone, pancreas, adrenal gland, esophagus, spine, testis, and bladder.

In another embodiment, the complement of the polynucleotide encoding GRBP or an antisense molecule may be administered to a subject to treat or prevent an immune disorder. Such disorders may include, but are not limited to, Sjögren's syndrome, Addison's disease, bronchitis, dermatomyositis, polymyositis, glomerulonephritis, diabetes mellitus, emphysema, Graves' disease, atrophic gastritis, lupus erythematosus, myasthenia gravis, multiple sclerosis, autoimmune thyroiditis, ulcerative colitis, anemia, pancreatitis, scleroderma, rheumatoid and osteoarthritis, asthma, allergic rhinitis, atopic dermatitis, dermatomyositis, polymyositis, and gout.

In another embodiment, antagonists or inhibitors of GRBP may be administered to a subject to treat or prevent any of the types of cancer listed above.

In another embodiment, antagonists or inhibitors of GRBP may be administered to a subject to treat or prevent any of the immune disorders listed above. In one aspect, antibodies which are specific for GRBP may be used directly as an antagonist, or indirectly as a targeting or delivery mechanism for bringing a pharmaceutical agent to cells or tissue which express GRBP.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of GRBP may be produced using methods which are generally known in the art. In particular, purified GRBP may be used to produce antibodies or to screen libraries of pharmaceutical agents to identify those which specifically bind GRBP.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with GRBP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to GRBP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of GRBP amino acids may be fused with those of another protein such as keyhole limpet hemocyanin and antibody produced against the chimeric molecule.

Monoclonal antibodies to GRBP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce GRBP-specific single chain antibodies. Antibodies with related specificity, but of distinct idiotypic composition, may be generated by chain shuffling from random combinatorial immunoglobelin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for GRBP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GRBP and its specific antibody. A two-site, monoclonal-based immunoassay utilizing monoclonal antibodies reactive to two non-interfering GRBP epitopes is preferred, but a competitive binding assay may also be employed (Maddox, supra).

In another embodiment of the invention, the polynucleotides encoding GRBP, or any fragment thereof, or antisense molecules, may be used for therapeutic purposes. In one aspect, antisense to the polynucleotide encoding GRBP may be used in situations in which it would be desirable to block the transcription of the mRNA. In particular, cells may be transformed with sequences complementary to polynucleotides encoding GRBP. Thus, antisense molecules may be used to modulate GRBP activity, or to achieve regulation of gene function. Such technology is now well known in the art, and sense or antisense oligomers or larger fragments, can be designed from various locations along the coding or control regions of sequences encoding GRBP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding GRBP. These techniques are described both in Sambrook et al. (supra) and in Ausubel et al. (supra).

Genes encoding GRBP can be turned off by transforming a cell or tissue with expression vectors which express high levels of a polynucleotide or fragment thereof which encodes GRBP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding GRBP, i.e., the promoters, enhancers, and introns. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding GRBP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GRBP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of GRBP, antibodies to GRBP, mimetics, agonists, antagonists, or inhibitors of GRBP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of GRBP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example GRBP or fragments thereof, antibodies of GRBP, agonists, antagonists or inhibitors of GRBP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio, LD50/ED50. Pharmaceutical compositions which exhibit large therapobtained from cell culture assays and aobtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind GRBP may be used for the diagnosis of conditions or diseases characterized by expression of GRBP, or in assays to monitor patients being treated with GRBP, agonists, antagonists or inhibitors. The antibodies useful for diagnostic purposes may be prepared in the same manner as those described above for therapeutics. Diagnostic assays for GRBP include methods which utilize the antibody and a label to detect GRBP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring GRBP are known in the art and provide a basis for diagnosing altered or abnormal levels of GRBP expression. Normal or standard values for GRBP expression are established by combining body fluids or cell extracts taken from normal mammalian subjects, preferably human, with antibody to GRBP under conditions suitable for complex formation. The amount of standard complex formation may be quantified by various methods, preferably by photometric, means. Quantities of GRBP expressed in subject, samples from biopsied tissues are compared with the standard values. Deviation between standard and subject values establishes the parameters for diagnosing disease.

In another embodiment of the invention, the polynucleotides encoding GRBP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of GRBP may be correlated with disease. The diagnostic assay may be used to distinguish between absence, presence, and excess expression of GRBP, and to monitor regulation of GRBP levels during therapeutic intervention.

In one aspect, hybridization with PCR probes which are capable of detecting polynucleotide sequences, including genomic sequences, encoding GRBP or closely related molecules, may be used to identify nucleic acid sequences which encode GRBP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding GRBP, alleles, or related sequences.

Probes may also be used for the detection of related sequences, and should preferably contain at least 50% of the nucleotides from any of the GRBP encoding sequences. The hybridization probes of the subject invention may be DNA or RNA and derived from the nucleotide sequence of SEQ ID NO:2 or from genomic sequence including promoter, enhancer elements, and introns of the naturally occurring GRBP.

Means for producing specific hybridization probes for DNAs encoding GRBP include the cloning of nucleic acid sequences encoding GRBP or GRBP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding GRBP may be used for the diagnosis of conditions or diseases which are associated with expression of GRBP. Examples of such conditions or diseases include disorders of the sympathetic nervous system such as hypertension, myocardial infraction, cardiovascular shock, angina, arrhythmias, asthma, migraine, anaphylactic shock, Cushing's syndrome, hypoglycemia, and pheochromocytoma; cancers such as cancer of the stomach, lung, heart, colon, cervix, ovaries, blood, intestine, prostate, uterus, breast, liver, spleen, brain, bone, pancreas, adrenal gland, esophagus, spine, testis, and bladder; and immunological disorders such as Sjögren's syndrome, Addison's disease, bronchitis, dermatomyositis, polymyositis, glomerulonephritis, diabetes mellitus, emphysema, Graves' disease, atrophic gastritis, lupus erythematosus, myasthenia gravis, multiple sclerosis, autoimmune thyroiditis, ulcerative colitis, anemia, pancreatitis, scleroderma, rheumatoid and osteoarthritis, asthma, allergic rhinitis, atopic dermatitis, dermatomyositis, polymyositis, and gout. The polynucleotide sequences encoding GRBP may be used in Southern or northern analysis, dot blot, or other membrane-based technologies; in PCR technologies; or in dip stick, pin, ELISA or chip assays utilizing fluids or tissues from patient biopsies to detect altered GRBP expression. Such qualitative or quantitative methods are well known in the art.

In a particular aspect, the nucleotide sequences encoding GRBP may be useful in assays that detect activation or induction of various cancers, particularly those mentioned above. The nucleotide sequences encoding GRBP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding GRBP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of GRBP, a normal or standard profile for expression is established. This may be accomplished by combining body fluids or cell extracts taken from normal subjects, either animal or human, with a sequence, or a fragment thereof, which encodes GRBP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GRBP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of GRBP include radiolabeling or biotinylating nucleotides, coamplification of a control nucleic acid, and standard curves onto which the experimental results are interpolated (Melby, P.C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode GRBP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome CDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding GRBP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, GRBP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between GRBP and the agent being tested, may be measured.

Another technique for drug screening which may be used provides for high throughput screening of compounds having suitable binding affinity to the protein of interest as described in published PCT application WO84/03564. In this method, as applied to GRBP large numbers of different small test compounds are synthesized on a solid substrate, such as plastic pins or some other surface. The test compounds are reacted with GRBP, or fragments thereof, and washed. Bound GRBP is then detected by methods well known in the art. Purified GRBP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GRBP specifically compete with a test compound for binding GRBP. In this manner, the antibodies can be used to detect the presence of any peptide which shares one or more antigenic determinants with GRBP.

In additional embodiments, the nucleotide sequences which encode GRBP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I PGANNOT03 cDNA Library Construction

The PGANNOT03 cDNA library was constructed from paraganlioma tissue obtained from a 46-year-old Caucasian male in the intra-abdominal region during nephroureterectomy and regional lymph node dissection for Grade 2 renal cell carcinoma. Initially, the patient presented with a headache, backache, nausea and vomiting. Subsequently, he was diagnosed with malignant neoplasm of kidney and malignant hypertension.

The frozen tissue was homogenized and lysed using a Polytron PT-3000 homogenizer (Brinkmann Instruments, Westbury N.J.) in guanidinium isothiocyanate solution. The lysate was centrifuged over a 5.7M CsCI cushion using an Beckman SW28 rotor in an L8-70M ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water and DNase treated at 37° C. RNA extraction and precipitation was repeated as before. The mRNA was then isolated using the OLIGOTEX kit (QIAGEN, Chatsworth, Calif.) and used to construct the cDNA library.

The mRNA was handled according to the recommended protocols in the SUPERSCRIPT plasmid system for cDNA synthesis and plasmid cloning (Cat. #18248-013, Gibco BRL, Gaithersburg, Md.). PGANNOT03 cDNAs were fractionated on a SEPHAROSE CL4B column (Cat. #275105-01, Pharmacia), and those cDNAs exceeding 400 bp were ligated into pINCY 1. The plasmid pINCY I was subsequently transformed into DH5α competent cells (Cat. #18258-012, Gibco/BRL).

II Isolation and Sequencing of cDNA Clones

Plasmid DNA was released from the cells and purified using the R.E.A.L. PREP 96 plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments.

BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding GRBP occurs. Abundance and percent abundance are also reported. Abundance directly reflects the number of times a particular transcript is represented in a cDNA library, and percent abundance is abundance divided by the total number of sequences examined in the cDNA library.

V Extension of GRBP-Encoding Polynucleotides to Full Length or to Recover Regulatory Sequences The nucleic acid sequence of Incyte clone 1291904 or SEQ ID NO:2 is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–23 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |

-continued

| Step 4 | 94° C. for 15 sec |
| --- | --- |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, or the blots are exposed to a Phosphoimager cassette (Molecular Dynamics, Sunnyvale, Calif.) hybridization patterns are compared visually.

VII Antisense Molecules

Antisense molecules to the GRBP-encoding sequence, or any part thereof, is used to inhibit in vivo or in vitro expression of naturally occurring GRBP. Although use of antisense oligonucleotides, comprising about 20 base-pairs, is specifically described, essentially the same procedure is used with larger cDNA fragments. An oligonucleotide based on the coding sequences of GRBP, as shown in FIGS. 1A, 1B and 1C is used to inhibit expression of naturally occurring GRBP. The complementary oligonucleotide is designed from the most unique 5' sequence as shown in FIGS. 1A, 1B and 1C and used either to inhibit transcription by preventing promoter binding to the upstream nontranslated sequence or translation of an GRBP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B and 1C.

VIII Expression of GRBP

Expression of GRBP is accomplished by subcloning the cDNAs into appropriate vectors and transforming the vectors into host cells. In this case, the cloning vector, pSport, previously used for the generation of the cDNA library is used to express GRBP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of GRBP into the bacterial growth media which can be used directly in the following assay for activity.

IX Demonstration of GRBP Activity

GRBP activity in the ras signaling pathway may be demonstrated by the ability of GRBP to stimulate mitogenesis in quiescent rat fibroblasts when co-microinjected with H-ras protein. Microinjections are performed with glass capillary pipettes drawn to a tip diameter of <1 mm. Approximately $10^{-11}$ mL of protein solution is injected/cell and 60–80 cells are injected within a defined area of the tissue culture dish. DNA synthesis is measured after addition and incorporation of the thymidine analog bromodeoxyuridine (BrdU) into mitogenic cells. After 24 hours of culture, the monolayer of cells is stained with anti-BrdU antibody. DNA synthesis in cultures co-injected with GRBP + H-ras is compared with that in control cultures (no injections or cultures injected with either GRBP or H-ras alone). A stimulation of at least 10-fold in DNA synthesis (BrdU incorporation) in GRBP + H-ras injected cells over and above control cultures indicates cooperative mitogenic activity of GRBP and H-ras in the ras signaling pathway.

X Production of GRBP Specific Antibodies

GRBP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc.) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring GRBP Using Specific Antibodies

Naturally occurring or recombinant GRBP is substantially purified by immunoaffinity chromatography using antibodies specific for GRBP. An immunoaffinity column is constructed by covalently coupling GRBP antibody to an activated chromatographic resin, such as CnBr-activated SEPHAROSE (Pharmacia & Upjohn). After the coupling, the resin is blocked and washed according to the manufacturer's instructions.

Media containing GRBP is passed over the immunoaffinity column, and the column is washed under conditions that allow the preferential absorbance of GRBP (e.g., high ionic strength buffers in the presence of detergent). The column is eluted under conditions that disrupt antibody/GRBP binding (eg, a buffer of pH 2–3 or a high concentration of a chaotrope, such as urea or thiocyanate ion), and GRBP is collected.

XII Identification of Molecules Which Interact with GRBP

GRBP or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled GRBP, washed and any wells with labeled GRBP complex are assayed. Data obtained using different concentrations of GRBP are used to calculate values for the number, affinity, and association of GRBP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide encoding a polypeptide comprising the amino acid sequence of SEQ ID NO:1.

2. An isolated and purified polynucleotide which hybridizes under stringent wash conditions of 0.1 x saline sodium citrate and 0.5% sodium dodecyl sulfate at room temperature to the polynucleotide of claim 1.

3. A hybridization probe comprising the polynucleotide of claim 1 and a detectable label.

4. An isolated and purified polynucleotide comprising SEQ ID NO:2.

5. An isolated and purified polynucleotide which is complementary to the polynucleotide of claim 1.

6. A hybridization probe comprising the polynucleotide of claim 5 and a detectable label.

7. An expression vector containing the polynucleotide of claim 1.

8. A host cell containing the expression vector of claim 7.

9. A method for producing a polypeptide comprising the amino acid sequence of SEQ ID NO:1, the method comprising the steps of:
 a) culturing the host cell of claim 8 under conditions suitable for the expression of the polypeptide; and
 b) recovering the polypeptide from the host cell culture.

10. A method for detection of a polynucleotide that hybridizes to the polynucleotide of SEQ ID NO:2 in a biological sample containing nucleic acid material, the method comprising the steps of:

a) hybridizing the polynucleotide of claim 5 to the nucleic acid material of the biological sample under stringent wash conditions of 0.1 x saline sodium citrate and 0.5% sodium dodecyl sulfate at room temperature, thereby forming a hybridization complex; and
 b) detecting the hybridization complex, wherein the presence of the hybridization complex correlates with the presence of a polynucleotide that hybridizes to the polynucleotide of SEQ ID NO:2.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 330 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: PGNNOT03
        ( B ) CLONE: 1291904

( x i ) SEQUENCE DESCRIPTION: SEQ ID NO:1:

```
Met  Glu  Ala  Val  Ala  Lys  Phe  Asp  Phe  Thr  Ala  Ser  Gly  Glu  Asp  Glu
 1                    5                              10                           15

Leu  Ser  Phe  His  Thr  Gly  Asp  Val  Leu  Lys  Ile  Leu  Ser  Asn  Gln  Glu
               20                              25                      30

Glu  Trp  Phe  Lys  Ala  Glu  Leu  Gly  Ser  Gln  Glu  Gly  Tyr  Val  Pro  Lys
               35                       40                      45
```

```
Asn  Phe  Ile  Asp  Ile  Gln  Phe  Pro  Lys  Trp  Phe  His  Glu  Gly  Leu  Ser
     50                       55                      60
Arg  His  Gln  Ala  Glu  Asn  Leu  Leu  Met  Asp  Lys  Glu  Val  Gly  Phe  Phe
65                       70                  75                           80
Ile  Ile  Arg  Ala  Ser  Gln  Ser  Ser  Pro  Gly  Asp  Phe  Ser  Ile  Ser  Val
                    85                       90                      95
Arg  His  Glu  Asp  Asp  Val  Gln  His  Phe  Lys  Val  Met  Arg  Asp  Asn  Lys
               100                      105                    110
Gly  Asn  Tyr  Phe  Leu  Trp  Thr  Glu  Lys  Phe  Pro  Ser  Leu  Asn  Lys  Leu
          115                      120                    125
Val  Asp  Tyr  Tyr  Arg  Thr  Asn  Ser  Ile  Ser  Arg  Gln  Lys  Gln  Ile  Phe
     130                      135                    140
Leu  Arg  Asp  Arg  Thr  Arg  Glu  Asp  Gln  Gly  His  Arg  Gly  Asn  Ser  Leu
145                      150                      155                         160
Asp  Arg  Arg  Ser  Gln  Gly  Gly  Pro  His  Leu  Ser  Gly  Ala  Val  Gly  Glu
                    165                      170                         175
Glu  Ile  Arg  Pro  Ser  Met  Asn  Arg  Lys  Leu  Ser  Asp  His  Pro  Pro  Thr
               180                      185                    190
Leu  Pro  Leu  Gln  Gln  His  Gln  His  Gln  Pro  Gln  Pro  Pro  Gln  Tyr  Ala
          195                      200                    205
Pro  Ala  Pro  Gln  Gln  Leu  Gln  Pro  Pro  Gln  Arg  Tyr  Leu  Gln
     210                      215                    220
His  His  His  Phe  His  Gln  Glu  Arg  Arg  Gly  Gly  Ser  Leu  Asp  Ile  Asn
225                      230                      235                         240
Asp  Gly  His  Cys  Gly  Thr  Gly  Leu  Gly  Ser  Glu  Met  Asn  Ala  Ala  Leu
                    245                      250                         255
Met  His  Arg  Arg  His  Thr  Asp  Pro  Val  Gln  Leu  Gln  Ala  Ala  Gly  Arg
               260                      265                    270
Val  Arg  Trp  Ala  Arg  Ala  Leu  Tyr  Asp  Phe  Glu  Ala  Leu  Glu  Asp  Asp
          275                      280                    285
Glu  Leu  Gly  Phe  His  Ser  Gly  Glu  Val  Val  Glu  Val  Leu  Asp  Ser  Ser
     290                      295                    300
Asn  Pro  Ser  Trp  Trp  Thr  Gly  Arg  Leu  His  Asn  Lys  Leu  Gly  Leu  Phe
305                      310                      315                         320
Pro  Ala  Asn  Tyr  Val  Ala  Pro  Met  Thr  Arg
                    325                      330
```

( 2 ) INFORMATION FOR SEQ ID NO:2:

( i ) SEQUENCE CHARACTERISTICS:
        ( A ) LENGTH: 1661 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: PGNNOT03
        ( B ) CLONE: 1291904

( x i ) SEQUENCE DESCRIPTION: SEQ ID NO:2:

```
GGGGCAGTGC   AAGCTTGCAT   GCCTGCAGGT   CGACTCTAGA   GGATCCCGGA   CTCTAGCCTA         60

GGCTTTTGCA   AAAAGCTATT   TAGGTGACAC   TATAGAAGGT   ACGCCTGCAG   GTACCGGTCC        120

GGAATTCCCG   GGTCGACCCA   CGCGTCCGGG   AGGAGGGAGT   AAGAGGTGGG   GAGGAGGAGG        180

CACAGTTAAT   GGATCTGTAA   ACTTGCACCC   TCTTTCAGAG   TGGTACATGG   AAGACAGCAC        240
```

```
AAAGTGGATC CATACTCTGA AATGCAGTAA CTCTGGTGCT TGAATTTGTC TCCCTTCTTG      300

CCAGAAAGGA TTCTAATAAC TCGGTGTCAA AGCCAAGACA TAAACTCAAC CCCTTCTCTT      360

CCAAAAGCTT CACGTTACAG CATGGAAGCT GTTGCCAAGT TTGATTTCAC TGCTTCAGGT      420

GAGGATGAAC TGAGCTTTCA CACTGGAGAT GTTTTGAAGA TTTTAAGTAA CCAAGAGGAG      480

TGGTTTAAGG CGGAGCTTGG GAGCCAGGAA GGATATGTGC CAAGAATTT CATAGACATC       540

CAGTTTCCCA AATGGTTTCA CGAAGGCCTC TCTCGACACC AGGCAGAGAA CTTACTCATG      600

GACAAGGAGG TTGGCTTCTT CATCATCCGG GCCAGCCAGA GCTCCCCAGG GGACTTCTCC      660

ATCTCTGTCA GGCATGAGGA TGACGTTCAA CACTTCAAGG TCATGCGAGA CAACAAGGGT      720

AATTACTTTC TGTGGACTGA GAAGTTTCCA TCCCTAAATA AGCTGGTAGA CTACTACAGG      780

ACAAATTCCA TCTCCAGACA GAAGCAGATC TTCCTTAGAG ACAGAACCCG AGAAGACCAG      840

GGTCACCGGG GCAACAGCCT GGACCGGAGG TCCCAGGGAG GCCCACACCT CAGTGGGGCT      900

GTGGGGAAG  AAATCCGACC TTCGATGAAC CGGAAGCTGT CGGATCACCC CCCGACCCTT      960

CCCCTGCAGC AGCACCAGCA CCAGCCACAG CCTCCGCAAT ATGCCCCAGC GCCCCAGCAG     1020

CTGCAGCAGC CCCCACAGCA GCGATATCTG CAGCACCACC ATTCCACCA GGAACGCCGA      1080

GGAGGCAGCC TTGACATAAA TGATGGGCAT TGTGGCACCG GCTTGGGCAG TGAAATGAAT     1140

GCGGCCCTCA TGCATCGGAG ACACACAGAC CCAGTGCAGC TCCAGGCGGC AGGGCGAGTG     1200

CGGTGGGCCC GGGCGCTGTA TGACTTTGAG GCCCTGGAGG ATGACGAGCT GGGGTTCCAC     1260

AGCGGGGAGG TGGTGGAGGT CCTGGATAGC TCCAACCCAT CCTGGTGGAC CGGCCGCCTG     1320

CACAACAAGC TGGGCCTCTT CCCTGCCAAC TACGTGGCAC CCATGACCCG ATAAACTCTT     1380

CAGGGGACAG AAGCTTTTTG TCTGGAGCTG CCCACAAGAA AGAGGGCAAG GAAGAAAGGC     1440

TGGACTCCAT GACTATATAT ACATACATCT ATCTACATCT GCCTGTGTAC ACACACAACT     1500

TTTTATACTA GTAATTTATT GCAATTGGGC TGGTAATTAG TTGATGCAAA AGGGAACTCA     1560

GGTGGAGAAT AATATTGACA CTTGCTTTTC TGCCCCCCTC AGGGGTGTGT GGAAGGCAGT     1620

GGGGGAGTTG GGAGGGGGGC AGGGAAATGA AATGGAGTTT T                         1661
```

(2) INFORMATION FOR SEQ ID NO:3:

(i) SEQUENCE CHARACTERISTICS:
        (A) LENGTH: 217 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 181976

(xi) SEQUENCE DESCRIPTION: SEQ ID NO:3:

```
Met Glu Ala Ile Ala Lys Tyr Asp Phe Lys Ala Thr Ala Asp Asp Glu
 1               5                  10                  15

Leu Ser Phe Lys Arg Gly Asp Ile Leu Lys Val Leu Asn Glu Glu Cys
             20                  25                  30

Asp Gln Asn Trp Tyr Lys Ala Glu Leu Asn Gly Lys Asp Gly Phe Ile
         35                  40                  45

Pro Lys Asn Tyr Ile Glu Met Lys Pro His Pro Trp Phe Phe Gly Lys
     50                  55                  60

Ile Pro Arg Ala Lys Ala Glu Glu Met Leu Ser Lys Gln Arg His Asp
65                  70                  75                  80
```

```
Gly  Ala  Phe  Leu  Ile  Arg  Glu  Ser  Glu  Ser  Ala  Pro  Gly  Asp  Phe  Ser
               85                      90                           95

Leu  Ser  Val  Lys  Phe  Gly  Asn  Asp  Val  Gln  His  Phe  Lys  Val  Leu  Arg
               100                     105                          110

Asp  Gly  Ala  Gly  Lys  Tyr  Phe  Leu  Trp  Val  Val  Lys  Phe  Asn  Ser  Leu
               115                     120                          125

Asn  Glu  Leu  Val  Asp  Tyr  His  Arg  Ser  Thr  Ser  Val  Ser  Arg  Asn  Gln
          130                      135                     140

Gln  Ile  Phe  Leu  Arg  Asp  Ile  Glu  Gln  Val  Pro  Gln  Gln  Pro  Thr  Tyr
145                           150                     155                     160

Val  Gln  Ala  Leu  Phe  Asp  Phe  Asp  Pro  Gln  Glu  Asp  Gly  Glu  Leu  Gly
                    165                      170                          175

Phe  Arg  Arg  Gly  Asp  Phe  Ile  His  Val  Met  Asp  Asn  Ser  Asp  Pro  Asn
               180                      185                          190

Trp  Trp  Lys  Gly  Ala  Cys  His  Gly  Gln  Thr  Gly  Met  Phe  Pro  Arg  Asn
               195                      200                     205

Tyr  Val  Thr  Pro  Val  Asn  Arg  Asn  Val
          210                 215
```

( 2 ) INFORMATION FOR SEQ ID NO:4:

( i ) SEQUENCE CHARACTERISTICS:
        ( A ) LENGTH: 217 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 55763

( x i ) SEQUENCE DESCRIPTION: SEQ ID NO:4:

```
Met  Glu  Ala  Ile  Ala  Lys  Tyr  Asp  Phe  Lys  Ala  Thr  Ala  Asp  Asp  Glu
1                   5                    10                          15

Leu  Ser  Phe  Lys  Arg  Gly  Asp  Ile  Leu  Lys  Val  Leu  Asn  Glu  Glu  Cys
               20                       25                          30

Asp  Gln  Asn  Trp  Tyr  Lys  Ala  Glu  Leu  Asn  Gly  Lys  Asp  Gly  Phe  Ile
          35                        40                         45

Pro  Lys  Asn  Tyr  Ile  Glu  Met  Lys  Pro  His  Pro  Trp  Phe  Phe  Gly  Lys
     50                        55                    60

Ile  Pro  Arg  Ala  Lys  Ala  Glu  Glu  Met  Leu  Ser  Lys  Gln  Arg  His  Asp
65                       70                      75                          80

Gly  Ala  Phe  Leu  Ile  Arg  Glu  Ser  Glu  Ser  Ala  Pro  Gly  Asp  Phe  Ser
               85                       90                          95

Leu  Ser  Val  Lys  Phe  Gly  Asn  Asp  Val  Gln  His  Phe  Lys  Val  Leu  Arg
               100                      105                         110

Asp  Gly  Ala  Gly  Lys  Tyr  Phe  Leu  Trp  Val  Val  Lys  Phe  Asn  Ser  Leu
               115                      120                         125

Asn  Glu  Leu  Val  Asp  Tyr  His  Arg  Ser  Thr  Ser  Val  Ser  Arg  Asn  Gln
          130                      135                     140

Gln  Ile  Phe  Leu  Arg  Asp  Ile  Glu  Gln  Val  Pro  Gln  Gln  Pro  Thr  Tyr
145                           150                     155                     160

Val  Gln  Ala  Leu  Phe  Asp  Phe  Asp  Pro  Gln  Glu  Asp  Gly  Glu  Leu  Gly
                    165                      170                          175

Phe  Arg  Arg  Gly  Asp  Phe  Ile  His  Val  Met  Asp  Asn  Ser  Asp  Pro  Asn
               180                      185                          190
```

```
Trp  Trp  Lys  Gly  Ala  Cys  His  Gly  Gln  Thr  Gly  Met  Phe  Pro  Arg  Asn
          195                      200                      205

Tyr  Val  Thr  Pro  Val  Asn  Arg  Asn  Val
          210                215
```

( 2 ) INFORMATION FOR SEQ ID NO:5:

( i ) SEQUENCE CHARACTERISTICS:
        ( A ) LENGTH: 228 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 134425

( x i ) SEQUENCE DESCRIPTION: SEQ ID NO:5:

```
Met  Glu  Ala  Val  Ala  Glu  His  Asp  Phe  Gln  Ala  Gly  Ser  Pro  Asp  Glu
1                        5                        10                       15

Leu  Ser  Phe  Lys  Arg  Gly  Asn  Thr  Leu  Lys  Val  Leu  Asn  Lys  Asp  Glu
               20                       25                       30

Asp  Pro  His  Trp  Tyr  Lys  Ala  Glu  Leu  Asp  Gly  Asn  Glu  Gly  Phe  Ile
          35                       40                       45

Pro  Ser  Asn  Tyr  Ile  Arg  Met  Thr  Glu  Cys  Asn  Trp  Tyr  Leu  Gly  Lys
     50                       55                       60

Ile  Thr  Arg  Asn  Asp  Ala  Glu  Val  Leu  Leu  Lys  Lys  Pro  Thr  Val  Arg
65                       70                       75                       80

Asp  Gly  His  Phe  Leu  Val  Arg  Gln  Cys  Glu  Ser  Ser  Pro  Gly  Glu  Phe
                    85                       90                       95

Ser  Ile  Ser  Val  Arg  Phe  Gln  Asp  Ser  Val  Gln  His  Phe  Lys  Val  Leu
               100                      105                      110

Arg  Asp  Gln  Asn  Gly  Lys  Tyr  Tyr  Leu  Trp  Ala  Val  Lys  Phe  Asn  Ser
          115                      120                      125

Leu  Asn  Glu  Leu  Val  Ala  Tyr  His  Arg  Thr  Ala  Ser  Val  Ser  Arg  Thr
     130                      135                      140

His  Thr  Ile  Leu  Leu  Ser  Asp  Met  Asn  Val  Glu  Thr  Lys  Phe  Val  Gln
145                      150                      155                      160

Ala  Leu  Phe  Asp  Phe  Asn  Pro  Gln  Glu  Ser  Gly  Glu  Leu  Ala  Phe  Lys
               165                      170                      175

Arg  Gly  Asp  Val  Ile  Thr  Leu  Ile  Asn  Lys  Asp  Asp  Pro  Asn  Trp  Trp
          180                      185                      190

Glu  Gly  Gln  Leu  Asn  Asn  Arg  Arg  Gly  Ile  Phe  Pro  Ser  Asn  Tyr  Val
          195                      200                      205

Cys  Pro  Tyr  Asn  Ser  Asn  Lys  Ser  Asn  Ser  Asn  Val  Ala  Pro  Gly  Phe
     210                      215                      220

Asn  Phe  Gly  Asn
225
```